United States Patent
Mizoguchi et al.

(10) Patent No.: US 6,434,416 B1
(45) Date of Patent: Aug. 13, 2002

(54) SURGICAL MICROSCOPE

(75) Inventors: Masakazu Mizoguchi, Tsukui-gun; Masahiko Kinukawa; Takashi Fukaya, both of Sagamihara, all of (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/435,597

(22) Filed: Nov. 8, 1999

(30) Foreign Application Priority Data

Nov. 10, 1998 (JP) .......................................... 10-319190

(51) Int. Cl.⁷ ................................................. A61B 5/05
(52) U.S. Cl. ...................... 600/427; 600/429; 600/471; 604/22; 359/372
(58) Field of Search ................................. 600/427, 429, 600/407, 471, 345; 604/22; 359/372

(56) References Cited

U.S. PATENT DOCUMENTS

| | | |
|---|---|---|
| 5,086,401 A | 2/1992 | Glassman et al. |
| 5,186,174 A * | 2/1993 | Schlondorff et al. |
| 5,273,039 A * | 12/1993 | Fujiwara et al. |
| 5,483,961 A * | 1/1996 | Kelly et al. |
| 5,579,772 A * | 12/1996 | Kinukawa et al. |
| 5,920,395 A * | 7/1999 | Schulz |
| 6,006,126 A * | 12/1999 | Cosman |
| 6,071,288 A * | 6/2000 | Carol et al. |
| 6,080,149 A * | 6/2000 | Huang et al. |
| 6,081,336 A * | 6/2000 | Messner et al. |

FOREIGN PATENT DOCUMENTS

| | | |
|---|---|---|
| DE | 196 40 993 | 4/1997 |
| JP | 3-205048 | 9/1991 |
| JP | 4-231034 | 8/1992 |
| JP | 5-305073 | 11/1993 |
| JP | 6-7335 | 1/1994 |
| JP | 6-175033 | 6/1994 |
| WO | WO 97/40763 | 11/1997 |

* cited by examiner

Primary Examiner—Marvin M. Lateef
Assistant Examiner—Jeoyuh Lin
(74) Attorney, Agent, or Firm—Frishauf, Holtz, Goodman & Chick, P.C.

(57) ABSTRACT

First sensing means senses the three-dimensional position of a microscope, with an operating site as the origin. Second sensing means senses the three-dimensional position of a surgical instrument with respect to the microscope. On the basis of the sensing results of the first sensing means and second sensing means, computing means calculates the three-dimensional position of the surgical instrument, with the operating site as the origin.

72 Claims, 13 Drawing Sheets

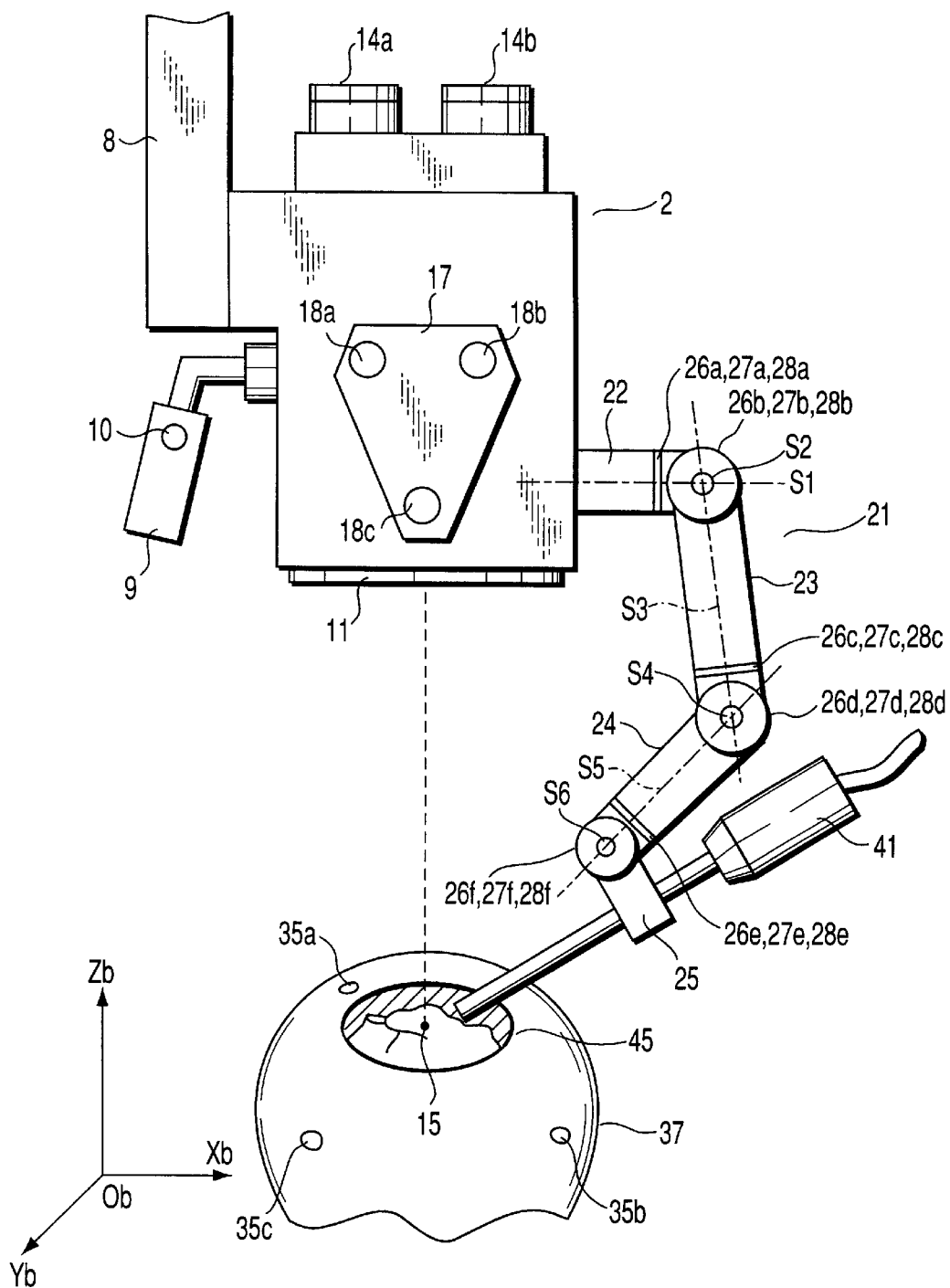
F I G. 2

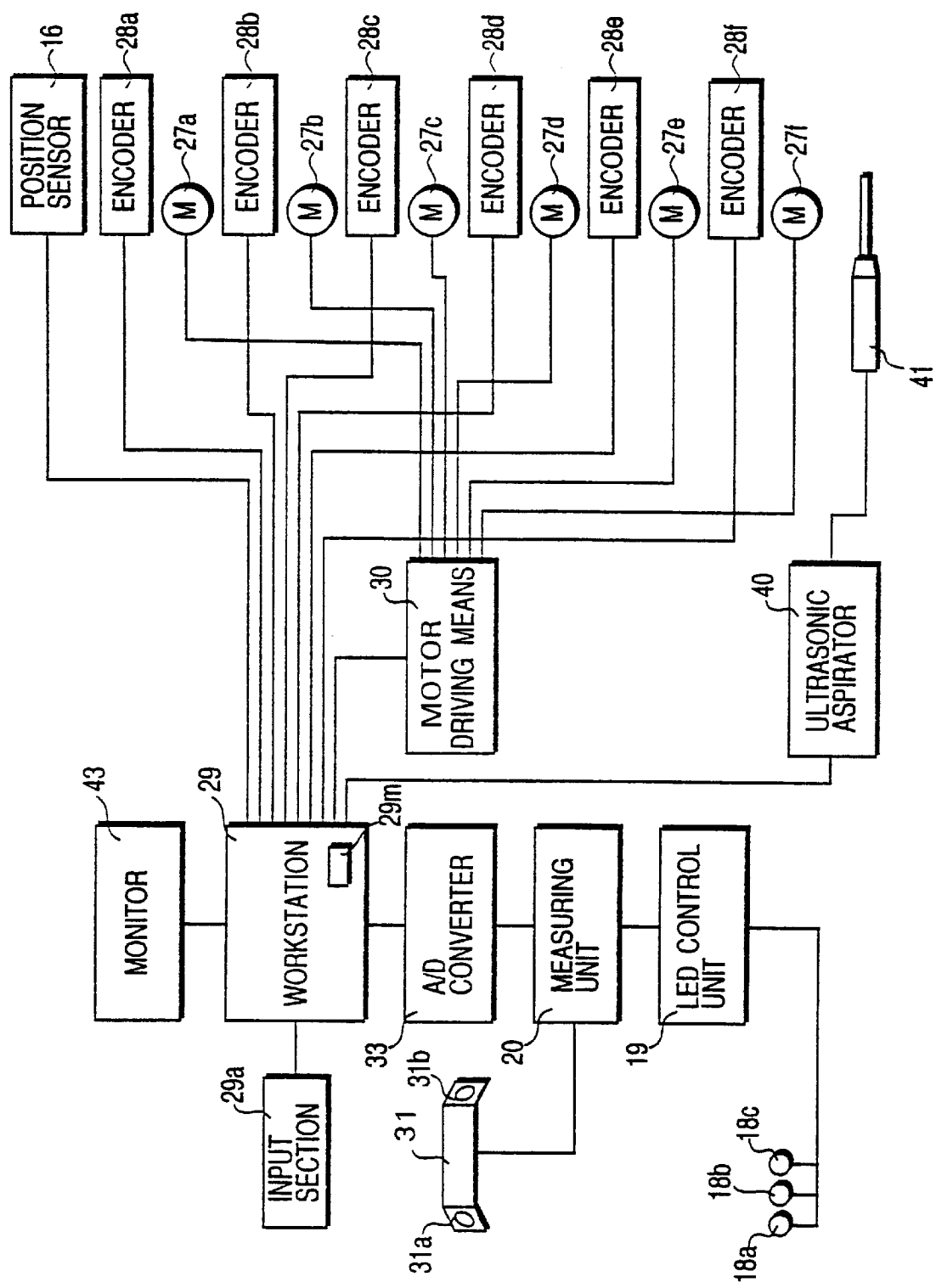
F I G. 4

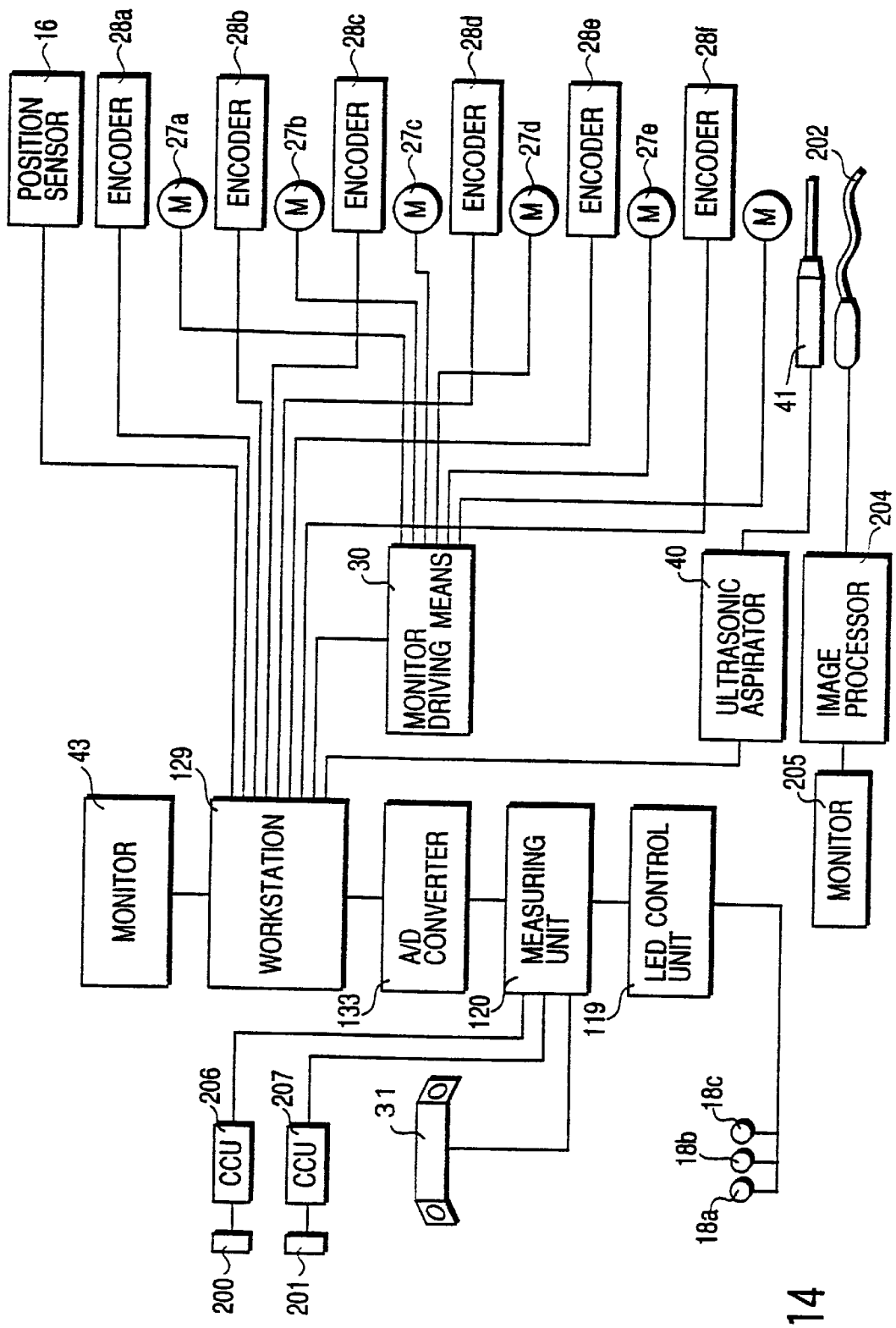
F I G. 14

SURGICAL MICROSCOPE

BACKGROUND OF THE INVENTION

This invention relates to a surgical microscope which enables the position of a medical instrument used under the surgical microscope to be sensed reliably.

In microsurgery where a fine operation is performed under a surgical microscope, before an operation, an operation plan has been made in recent years on the basis of tomographic images. In addition, surgical instruments have been undergoing improvement with an eye to making effective use of the tomographic information even during the operation to assure a safe operation.

In the field of brain surgery in particular, the observation position under a surgical microscope has been sensed on the basis of tomographic images before an operation and the tomographic image information corresponding to the observation position under the microscope has been obtained.

In the prior art, for example, Jpn. Pat. Appln. KOKAI Publication No. 3-205048 has disclosed the technique for sensing the observation position under a surgical microscope. Jpn. Pat. Appln. KOKAI Publication No. 5-305073 has disclosed means for sensing the operating position as well as the surgical microscope. Jpn. Pat. Appln. KOKAI Publication No. 6-175033 has disclosed position determining means for determining the position within or near the observation visual field. In addition, Jpn. Pat. Appln. KOKAI Publication No. 4-231034 has disclosed the technique for sensing and controlling the position of a surgical instrument by means of a robot manipulator.

A system for integrating the observed site into the tomographic image before the operation has been disclosed as means for sensing the positions of an endoscope, a treating instrument, and a surgical microscope.

In Jpn. Pat. Appln. KOKAI Publication No. 3-205048 and Jpn. Pat. Appln. KOKAI Publication No. 4-231034, to sense a position three-dimensionally by means of the body tube supporting arm of a surgical microscope, a second support arm for supporting the treating instrument or endoscope and sensing the position three-dimensionally or an optical position sensing device had to be installed additionally in an operating room, even when the position of the treating instrument or endoscope was sensed under the microscope. Consequently, the second support arm or position sensing device occupied the operating room additionally.

In Jpn. Pat. Appln. KOKAI Publication No. 5-305073, when the position of the endoscope or treating instrument was sensed together with the microscope, the operating site was complicated, because the microscope tube, operator, other treating instruments, and medical instruments were arranged there. Moreover, the treating instrument or endoscope used under the microscope was often unable to sense the position because the medical instruments positioned near the microscope, the hands and arms of the operator, and the operating site intervened between the signal member and the digitizer.

When the digitizer was installed in an operating room to sense the position of the treating instrument, it was necessary to leave a specific space between indexes marked on the treating instrument. If such a space could not be left, it would be impossible to sense the position because the digitizer picked up the indexes repeatedly. An attempt to overcome the drawback causes the problem of enlarging the indexes marked on the treating instrument.

In Jpn. Pat. Appln. KOKAI Publication No. 6-175033, the body tube is moved according to the indication of the observed site, but the site is not correlated to the tomographic image before the operation. Therefore, it is impossible to correlate the tomographic image with the three-dimensional position in the observation visual field of the microscope. Moreover, it is impossible for the treating instrument connected to the manipulator to control the manipulator and give treatments.

BRIEF SUMMARY OF THE INVENTION

The object of the present invention is to provide a surgical microscope capable of sensing a three-dimensional relative position with respect to the microscope within or near the observation visual field.

The foregoing object is accomplished by providing a surgical microscope comprising: first sensing means for sensing the three-dimensional position of a microscope, with an operating site as the origin; second at least one first sensing means for sensing the three-dimensional position of a surgical instrument with respect to the microscope; and computing means for calculating the three-dimensional position of the surgical instrument, with the operating site as the origin, on the basis of the sense results of the first sensing means and second sensing means.

With this configuration, use of the means for sensing the three-dimensional position of the microscope and the means for sensing a three-dimensional position using the microscope as a reference in the surgical microscope makes it possible to sense three-dimensional coordinates in the observation visual field or near the body tube in the form of the relative position to the body tube and convert the position into coordinates on the coordinate system by the means for sensing the three-dimensional position of the microscope. This shortens the operating time and alleviates the fatigue of the operator.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2 is an enlarged side view of the body tube section of the first embodiment;

FIG. 4 is a block diagram showing the functional configuration of the entire surgical microscope according to the first embodiment;

FIG. 14 is a block diagram showing the functional configuration of the entire surgical microscope according to the fourth embodiment.

DETAILED DESCRIPTION OF THE INVENTION

Hereinafter, referring to the accompanying drawings, embodiments of the present invention will be explained.

Figure 1:
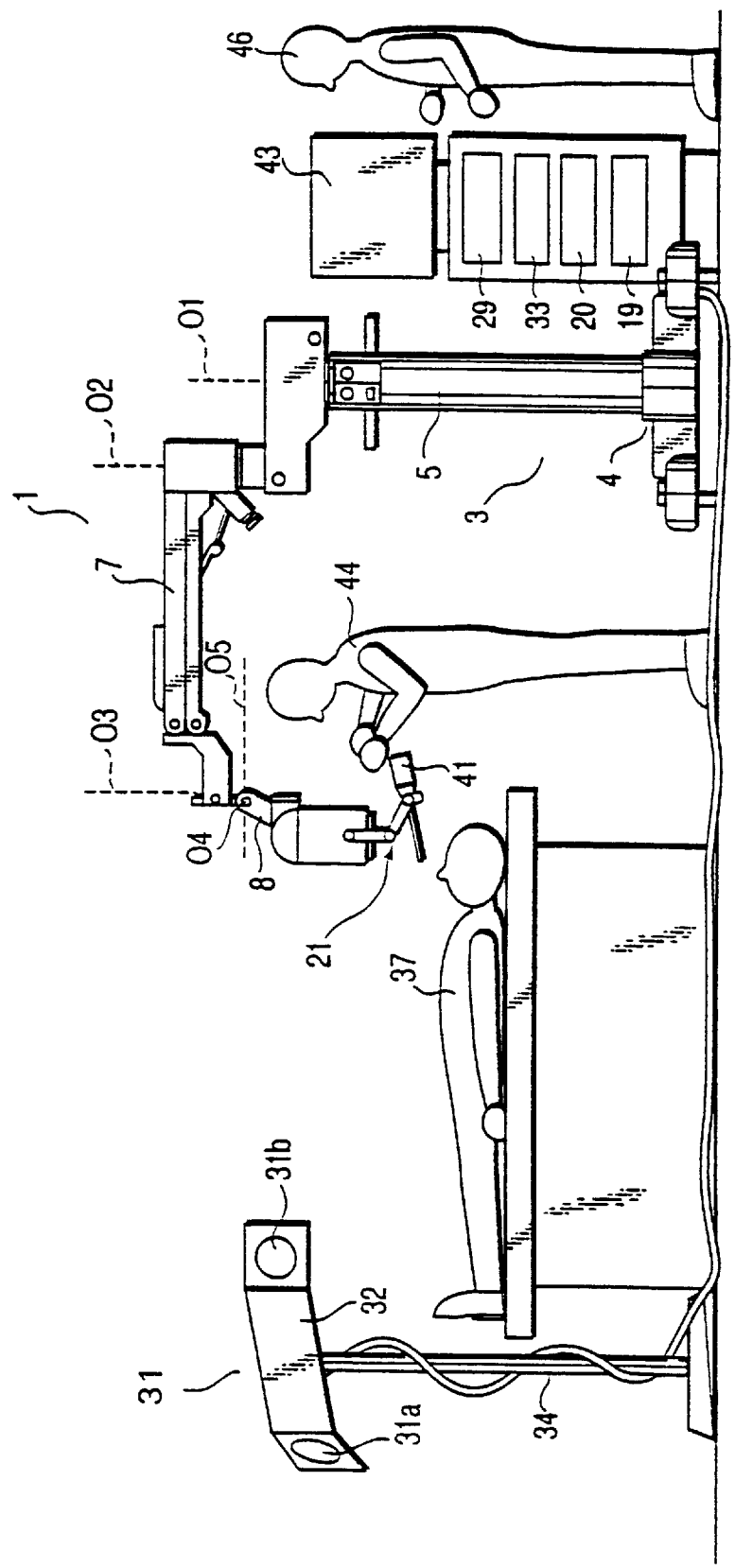
FIG. 1 schematically shows the configuration of a whole surgical microscope according to a first embodiment of the present invention.
Figure 3:
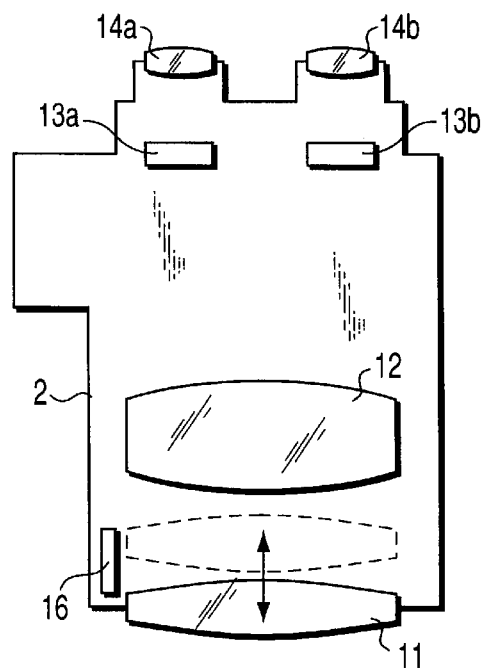
FIG. 3 is a sectional view showing the internal configuration of the microscope section of the first embodiment.
Figure 5:
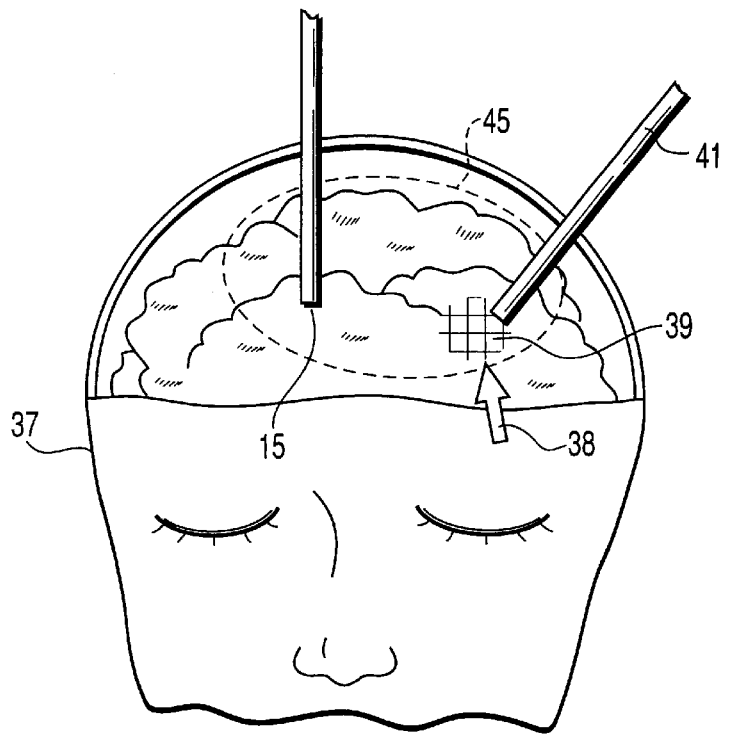
FIG. 5 shows an example of an image displayed on the monitor of the workstation in the first embodiment.

FIG. 1 schematically shows the configuration of a whole surgical microscope according to a first embodiment of the present invention. FIG. 2 is an enlarged side view of the microscope section. FIG. 3 is a sectional view showing the internal configuration of the microscope section. FIG. 4 is a block diagram showing the functional configuration of the entire surgical microscope. FIG. 5 shows an example of an image displayed on the monitor of the workstation.

In the surgical microscope of FIG. 1, a pedestal 3 includes a base 4 capable of moving over the floor surface and a pillar 5 set up straight on the base 4. At the upper part of the pillar 5, one end of a first arm 6 in which an illumination light source (not shown) is incorporated is provided in such a manner that it rotates freely on axis O1.

At the other end of the first arm 6, one end of a second arm 7 is provided in such a manner that it rotates freely on axis O2. The second arm 7 is a pantograph arm composed of a link mechanism and a balance adjusting spring member to make up-and-down movements. A third arm 8 is provided at the other end of the second arm 7 in such a manner that it can rotate freely on axis O3. The third arm 8 is an arm designed to enable the microscope 2 to incline forward and backward, centering on axis O4, in the direction of observation of the operator and look to the right and to the left of the operator, centering on axis 05. The microscope 2 is provided at the other end of the third arm 8.

Furthermore, an electromagnetic brake (not shown) is provided at each of the rotating sections of the rotating axes O1 to O5. The electromagnetic brakes are used to adjust the position of the microscope 2 freely in three dimensions and fix the position. The electromagnetic brakes are connected to an electromagnetic brake power-supply circuit (not shown) built in the pillar 5. The electromagnetic brake power-supply circuit is connected to a switch 10 provided on a grip 9 secured integrally to the microscope 2.

As shown in FIG. 3, the microscope 2 includes an objective 11, a variable power optical system 12, a pair of image-forming lenses 13a, 13b, and a pair of eyepieces 14a, 14b, which are arranged in that order on the observation optical axis extending from the operating site and constitute a stereoscopic observation optical system.

The image-forming surface made by the image-forming lenses 13a, 13b are so placed that they are at the position of the focal point of each of the eyepieces 14a, 14b, respectively. In FIG. 2, numeral 15 indicates the position of the focal point of the microscope 2. The objective 11 is coupled with a motor (not shown). It is designed to be movable in the direction of optical axis and able to sense the lens position by means of a position sensor 16.

Numeral 17 indicates a signal plate used for the digitizer to sense the three-dimensional coordinates of the microscope 2. Three LEDs 18a, 18b, and 18c, signal members, are fixed integrally to the signal plate 17. As shown in FIG. 4, the LEDs 18a, 18b, and 18c are connected to an LED control unit 19. The LED control unit 19 is connected to a measuring unit 20. The signal plate 17 is positioned in a specific position on the side face of the microscope 2 and fixed integrally to the microscope 2.

In FIG. 2, numeral 21 indicates a robot manipulator. The robot manipulator 21 includes a first arm 22, a second arm 23, a third arm 24, a treating instrument connection 25 capable of gripping the treating instrument at its end, and rotatable joints 26a to 26f. In the first embodiment, a probe 41 connected as a treating instrument to an ultrasonic aspirator 40 is secured in a detachable manner.

One end of the first arm 22 is fixed integrally to the microscope 2. The first arm 22 is coupled with the second arm 23 via the joint 26a with axis S1 as the axis of rotation and the joint 26b with axis S2 perpendicular to the sheet of paper as the axis of rotation. Similarly, the second arm 23 is coupled with the third arm 24 via the joint 26c with axis S3 as the axis of rotation and the joint 26d with axis S4 perpendicular to the sheet of paper as the axis of rotation. In addition, the third arm 24 is coupled with the treating instrument connection 25 via the joint 26e with axis S5 as the axis of rotation and the joint 26f with axis S6 perpendicular to the sheet of paper as the axis of rotation.

The joints 26a to 26f have encoders 28a to 28f and motors 27a to 27f shown in FIG. 4, respectively. The encoders 28a to 28f are connected to a workstation 29. The motors 27a to 27f are connected to motor driving means 30 provided inside the pillar The motor driving means 30 is connected to the workstation 29.

The treating instrument connection 25 is positioned in a specific position of the probe 41 and coupled detachably with the probe. The probe 41 is connected to the ultrasonic aspirator 40 as shown in FIG. 4. The ultrasonic aspirator 40 is connected to the workstation 29.

Numeral 31 indicates a digitizer (or optical position sensing device) for sensing the positions of the LEDs 18a, 18b, and 18c on three-dimensional coordinate axes. The digitizer 31 is composed of two CCD cameras 31a, 31b as reception members, a camera support member 32 for holding the CCD cameras 31a, 31b in place, and a stand 34. The digitizer is installed in an operating room. The CCD cameras 31a, 31b are connected to the measuring unit 20. The measuring unit 20 is connected to the workstation 29 via an A/D converter 33.

A monitor 43 and an input section 29i are connected to the workstation 29. In the workstation, a memory 29m stores the tomographic image data from an image diagnostic unit (not shown), such as CT or MRI, before an operation, and the data obtained by processing the tomographic image data and reconstructing it into three-dimensional data.

Reference symbols 35a, 35b, 35c indicate mark members stuck to a patient 37 to be treated. Ob-XbYbZb is a living body coordinate system defined on the basis of the mark members 35a, 35b, 35c. Namely, it is a coordinate system using the operating site as the origin.

FIG. 5 shows an image displayed on the monitor screen. The focal point position 15 of the surgical microscope 1 and the tip of the probe 41 are superimposed on the image reconstructed three-dimensionally on the basis of the tomographic image before the operation of the patient 37. Numeral 38 indicates the mouse pointer specified by the mouse provided for the input section 29i. Numeral 39 indicates the extirpating range, the target site, entered from the mouse pointer 38.

Figure 6:
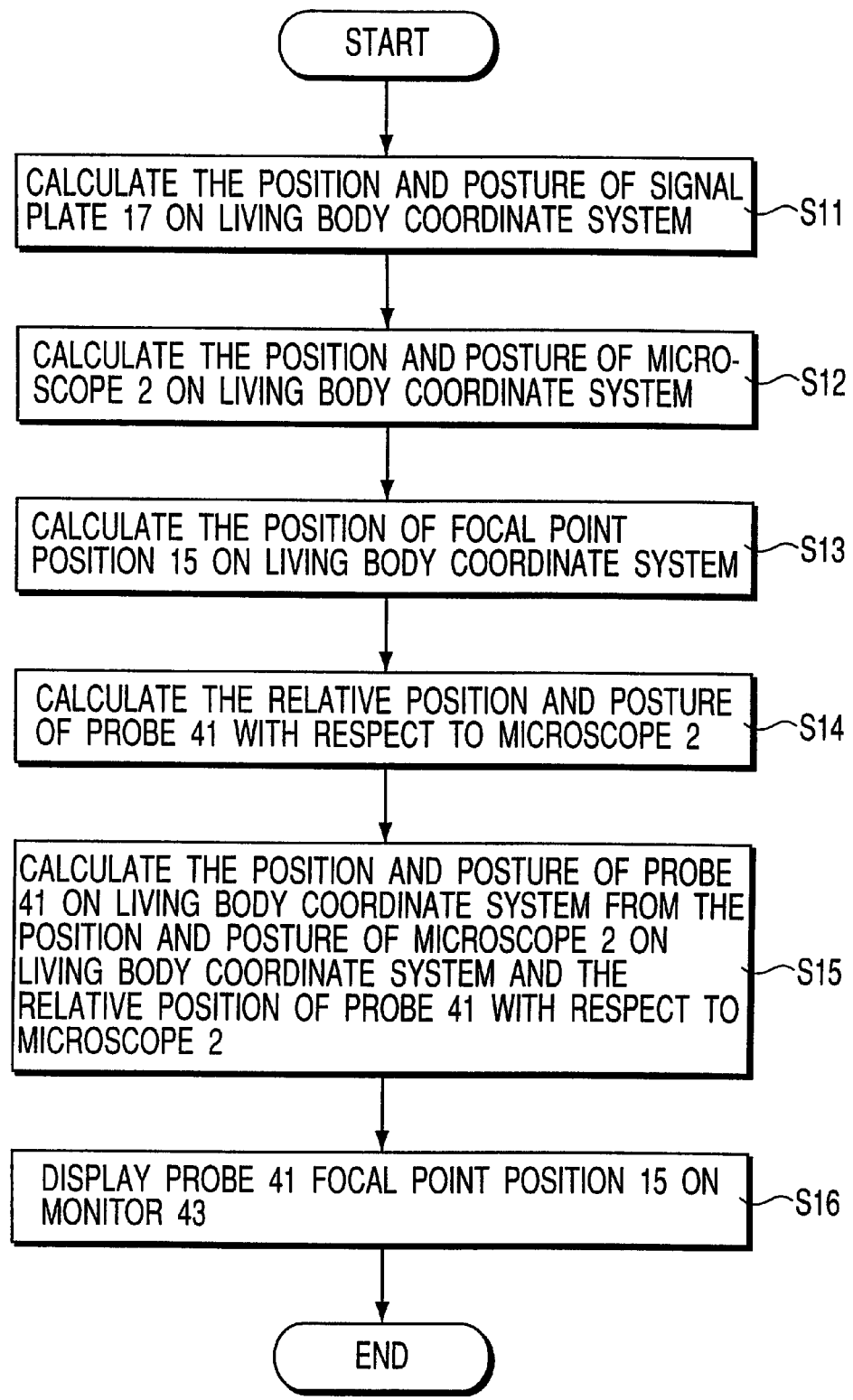
FIG. 6 is a flowchart to help explain the operation of the first embodiment.

Next, the operation of the first embodiment will be explained by reference to the flowchart of FIG. 6.

The tomographic images obtained beforehand from such a machine as CT or MRI is reconstructed into three-dimensional data before an operation. The three-dimensional data is stored in the memory 29m of the workstation 29. Before the operation, calibration, or the living body coordinate system Ob-XbYbZb, is memorized using the mark members 35a, 35b, 35c in such a manner that the tomographic image data in the workstation 29 is correlated to the coordinates of the operating site.

As a result of the work, the living body coordinate system is stored in the workstation 29. The three-dimensional data on the monitor 43 is displayed as an image on the living body coordinate system on the monitor 43.

The operator 44 grasps the grip 9 and presses the switch 10, thereby releasing the electromagnetic brakes built in the axes O1 to O5. This moves the microscope 2 and sets the focal point position 15 in the observation region of the operating site 45.

The luminous flux emitted from the operating site enters the microscope 2. The luminous flux passed through the objective 11 and arrived at the microscope 2 passes through the variable power optical system 12, image-forming lenses 13a, 13b, and eyepieces 14a, 14b, and is then observed. The operator 44 observes the operating site at the desired magnification. When the focal point position of the observed image is out of focus, the objective 11 is driven by a motor (not shown) to bring the focal point position into focus.

The digitizer 31 senses the LEDs 18a, 18b, 18c on the signal plate 17. The measuring unit 20 and A/D converter 33 process the signal and the workstation 29 calculates the position and posture of the signal plate 17 on the living body coordinate system (step S11). Since the signal plate 17 has been provided in a specific position on the microscope 2, the position and posture of the microscope 2 on the living body coordinate system are calculated (step S12).

The position sensor 16 transmits position information on the objective 11 to the workstation 29. The workstation 29 calculates the relative position of the focal point position 15 to the microscope 2 from position information on the objective 11.

The position of the focal point position 15 on the living body coordinate system is calculated from the position and posture of the microscope 2 on the living body coordinate system and the relative position of the focal point position 15 to the microscope 2 (step S13). The three-dimensional data and focal point position are superimposed on the displayed living body coordinate system on the monitor 43.

Because the focal point position 15 is displayed on the monitor 43 in such a manner that it is superimposed on the image based on the three-dimensional image data, the operator 44 can know the observation position under the microscope on the image based on the three-dimensional data. This is a known technique.

The position of the tip of the probe 41 on the living body coordinate system is calculated as follows. The encoders 28a to 28f transmit the respective rotational angles of the joints 26a to 26f of the robot manipulator 21 to the workstation 29. Using a generally known mathematical approach, the workstation 29 calculates the position of the second arm 23 to the first arm 22 fixed to the microscope 2, the position of the third arm 24 to the second arm 23, and the position of the treating instrument connection 25 to the third arm 24.

Since the treating instrument connection 25 secures the probe 41 in a specific position, the relative position and posture of the tip of the probe 41 to the microscope 2 are calculated from the length from the specific position of the probe 41 to its tip (step S14). Because the position of the microscope 2 on the living body coordinate system is known, the coordinates and posture of the tip of the probe 41 on the living body coordinate system are calculated (step S15). Then, the tip of the probe 41 and the focal point position 15 are displayed on the monitor 43 as shown in FIG. 5 (step S16).

Figure 7:
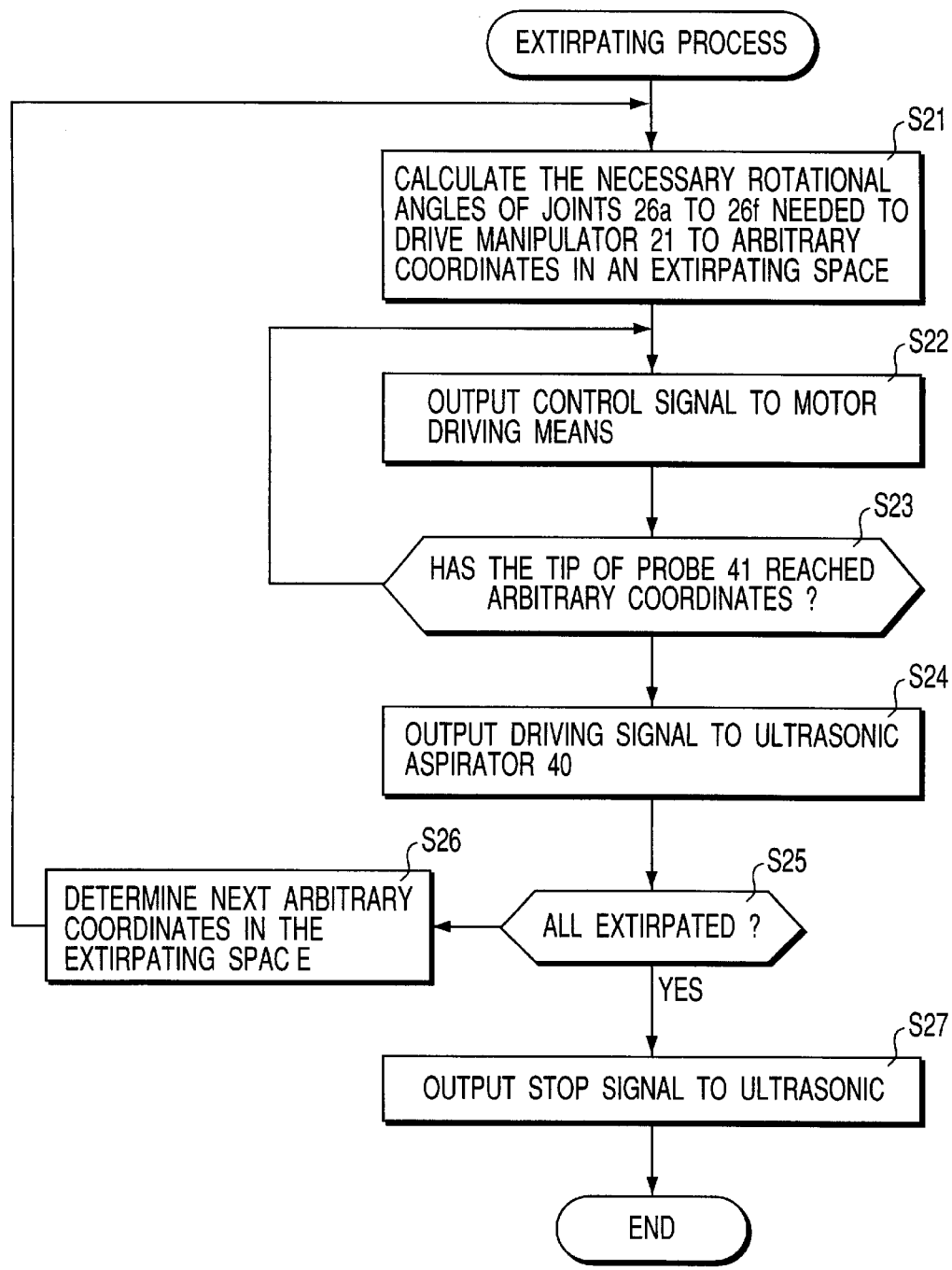
FIG. 7 is a flowchart to help explain the operation of the first embodiment.

Furthermore, the operation of moving the ultrasonic aspirator 41 to the desired position and controlling the aspirator by means of the robot manipulator 21 will be explained by reference to the flowchart in FIG. 7.

First, the operator 46 enters the extirpating range 39 on the monitor 43 with the mouse pointer 38 and the depth of extirpating section from the input section 29a. After having entered the data items, the operator clicks the switch on the monitor (not shown) with the mouse, thereby starting the process of driving the robot manipulator 21.

The workstation 29 calculates the necessary rotational angles of the joints 26a to 26f to drive the robot manipulator 21 from the tip of the probe 41 at the time of starting the driving process to arbitrary coordinates in the extirpating space (step S21). In addition, the workstation 29 calculates the pulses of the encoders 28a to 28f from the rotational angles and outputs a control signal to the motor driving means 30 on the basis of the calculation result.

The motor driving means 30 outputs the corresponding driving signals to the motors 27a to 27f. It is judged whether the tip of the probe 41 has reached arbitrary coordinates in the extirpating space (step S23). If the judgment at step S23 has shown YES, the workstation 29 further outputs a driving signal to the ultrasonic aspirator 40, thereby starting aspiration with the probe 41 (step S24).

Furthermore, the workstation 29 judges whether all the extirpating space entered has been removed (step S25). If the judgment at step S25 has shown NO, next arbitrary coordinates in the extirpating space are so determined that the robot manipulator 21 is driven in such a manner that the prove 41 moves all over the extirpating space (step S26). Then, the workstation outputs control signals for the motors 27a to 27f to the motor driving means 30 on the basis of the rotational angles from the encoders 28a to 28f for the joints 26a to 26f (step S22).

The workstation 29 repeats the above operation until the tip of the probe 41 has moved all over the extirpating space entered on the monitor. Thereafter, the judgment at step S25 has shown YES, and the workstation outputs a stop signal to the ultrasonic aspirator (step S27). The probe 41 moves the robot manipulator 21 to the position of the starting point of the series of processes, which completes the extirpating process.

With the first embodiment, since the position of the tip of the probe 41 of the treating instrument (ultrasonic aspirator) is sensed in the form of a relative position to the microscope 2, the position of the treating instrument can be sensed easily even near the complicated operating site, which shortens the operating time and alleviates the operator's fatigue. Because there is no need to pick up the probe with the digitizer, this gives more flexibility to the installation of the digitizer, which makes it possible to use the limited operating space more effectively.

Furthermore, since the instrument can be moved precisely by entering the data using the mouse or keyboard on the computer, while checking the image diagnostic data before the operation, the difference in skill between operators is absorbed, which not only enables more accurate operations but also alleviates the burden on the patient.

Figure 8:
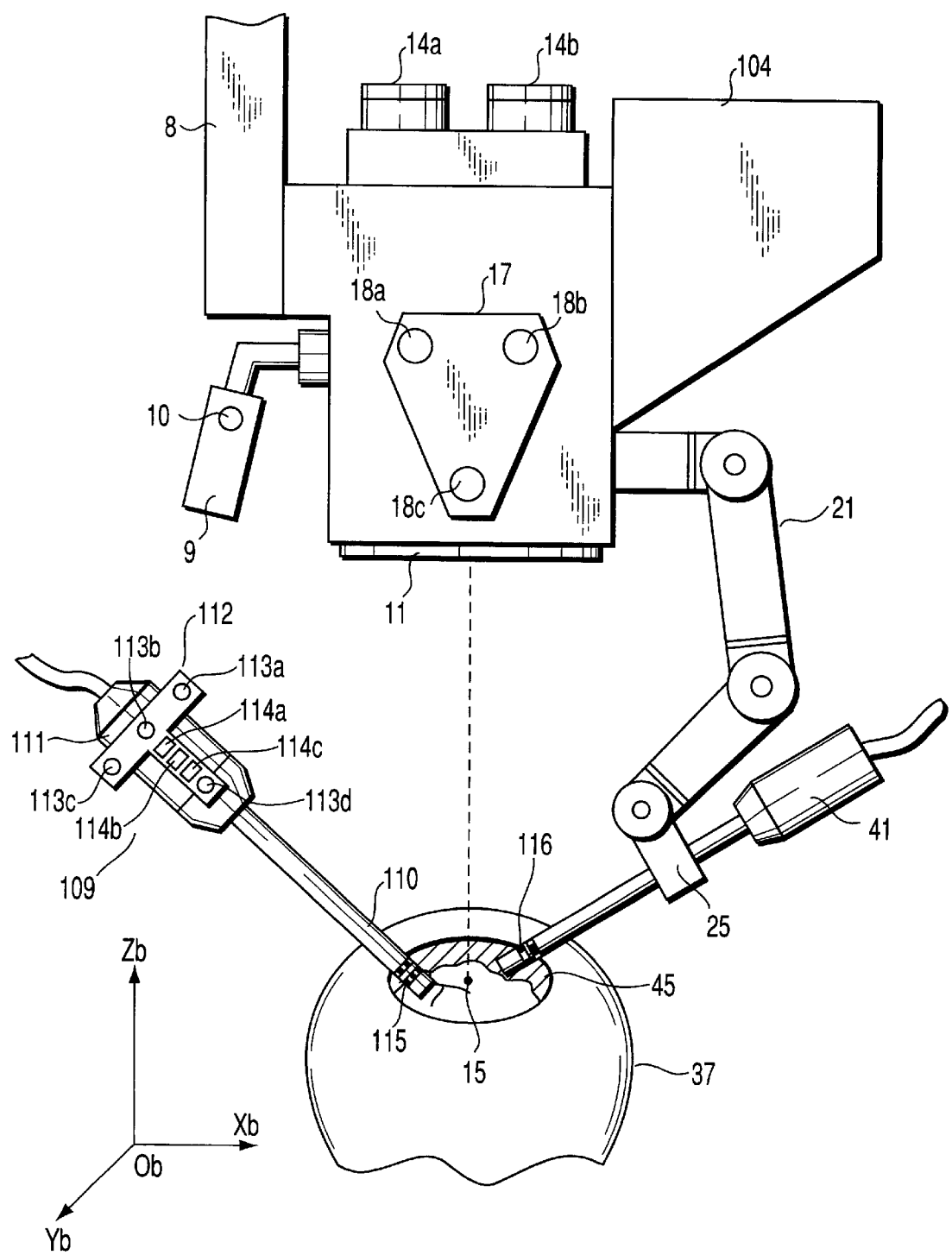
FIG. 8 is an enlarged side view of a body tube section according to a second embodiment of the present invention.
Figure 9:
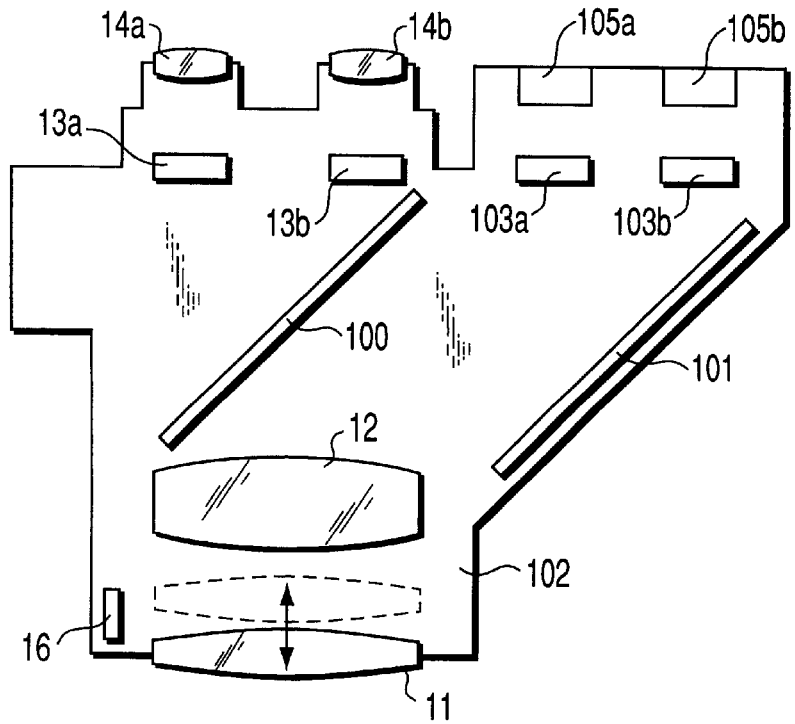
FIG. 9 is a sectional view showing the internal configuration of the microscope section of the second embodiment.
Figure 11B:
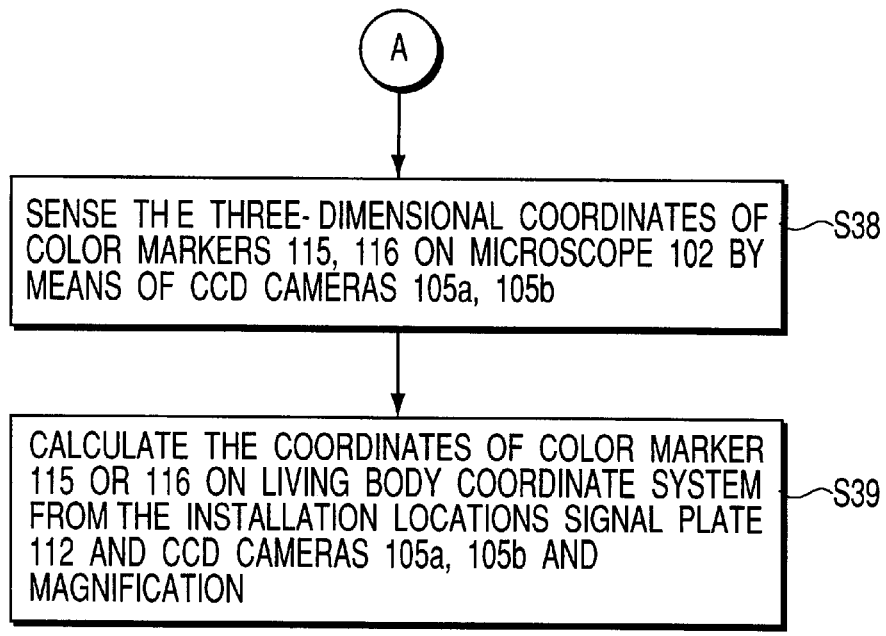
FIGS. 11A and 11B are flowcharts to help explain the operation of the second embodiment.
Figure 10:
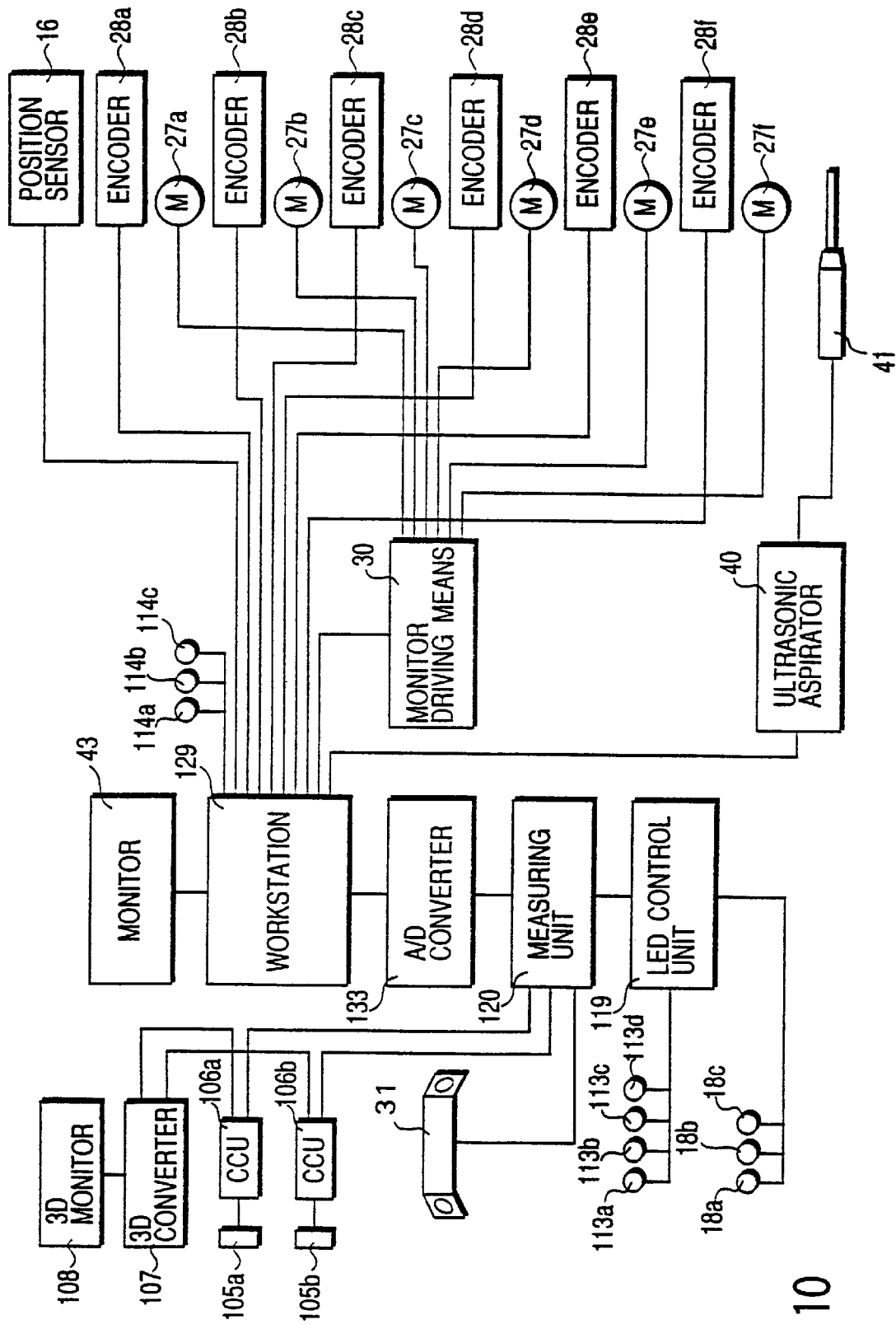
FIG. 10 is a block diagram showing the functional configuration of the entire surgical microscope according to the second embodiment.

Next, FIGS. 8 to 11B are related to a second embodiment of the present invention. FIG. 8 is an enlarged side view of a body tube section according to the second embodiment. FIG. 9 is a sectional view showing the internal configuration of the body tube section. FIG. 10 is a block diagram showing the functional configuration of the entire surgical microscope. FIGS. 11A and 11B are flowcharts to help explain the operation of the second embodiment.

In FIGS. 8 to 10, the same parts as those in the first embodiment are indicated by the same reference symbols and a detailed explanation of them will not be given.

In FIGS. 8 and 9, a body tube 102 includes a variable power optical system 12 and a half mirror 100 provided between a pair of image-forming lenses 13a, 13b which deflects part of luminous flux at right angles sideways. There is also provided a mirror 101 for deflecting the deflected luminous flux upward again. Reference symbols 103a, 103b indicate a pair of image-forming lenses for making an image from the deflected luminous flux. Magnification sensing means (not shown) is connected to the variable power optical system 12. The magnification sensing means is connected to the workstation 129.

A camera box 104 is provided in a specific position on the microscope 102. CCD cameras 105a and 105b are built in the camera box 104. The CCD cameras 105a, 105b are fixed integrally in a specific position on the camera box in such a manner that the cameras 105a, 105b are located in the image-forming planes by the image-forming lenses 103a, 103b, respectively.

The CCD cameras 105a, 105b are connected to CCUs 106a, 106b, respectively. The CCUs 106a, 106b are connected to a 3D converter 107. The 3D converter 107 is connected to a 3D monitor 108. The CCUs 106a, 106b are connected to a measuring unit 120. The measuring unit 120 is connected to the workstation 129 via an A/D converter 133.

Numeral 109 indicates a rigid endoscope and numeral 110 indicates the insert section of the rigid endoscope 109. Numeral 111 indicates a CCD camera for picking up the image picked up by the rigid endoscope 109. Numeral 112 indicates a signal plate fixed detachably in a specific position on the endoscope 109. LEDs 113a to 113d are secured to the signal plate. The LEDs 113a to 113d are connected to an LED control unit 119.

The signal plate 112 is further provided with luminous setting switches 114a, 114b, and 114c. The setting switches 114a, 114b, 114c are connected to the workstation 129. The workstation 129 records the type of the treating instrument to which the signal plate has been installed, the state of installation, and the position of the tip of the treating instrument, by means of the setting switches 114a, 114b, 114c on the signal plate 112.

Numeral 115 is a color marker provided at the tip of the insert section 110. Numeral 116 is a color marker provided at the tip of the probe 41, which differs from the color marker 115 in color arrangement.

Figure 11A:
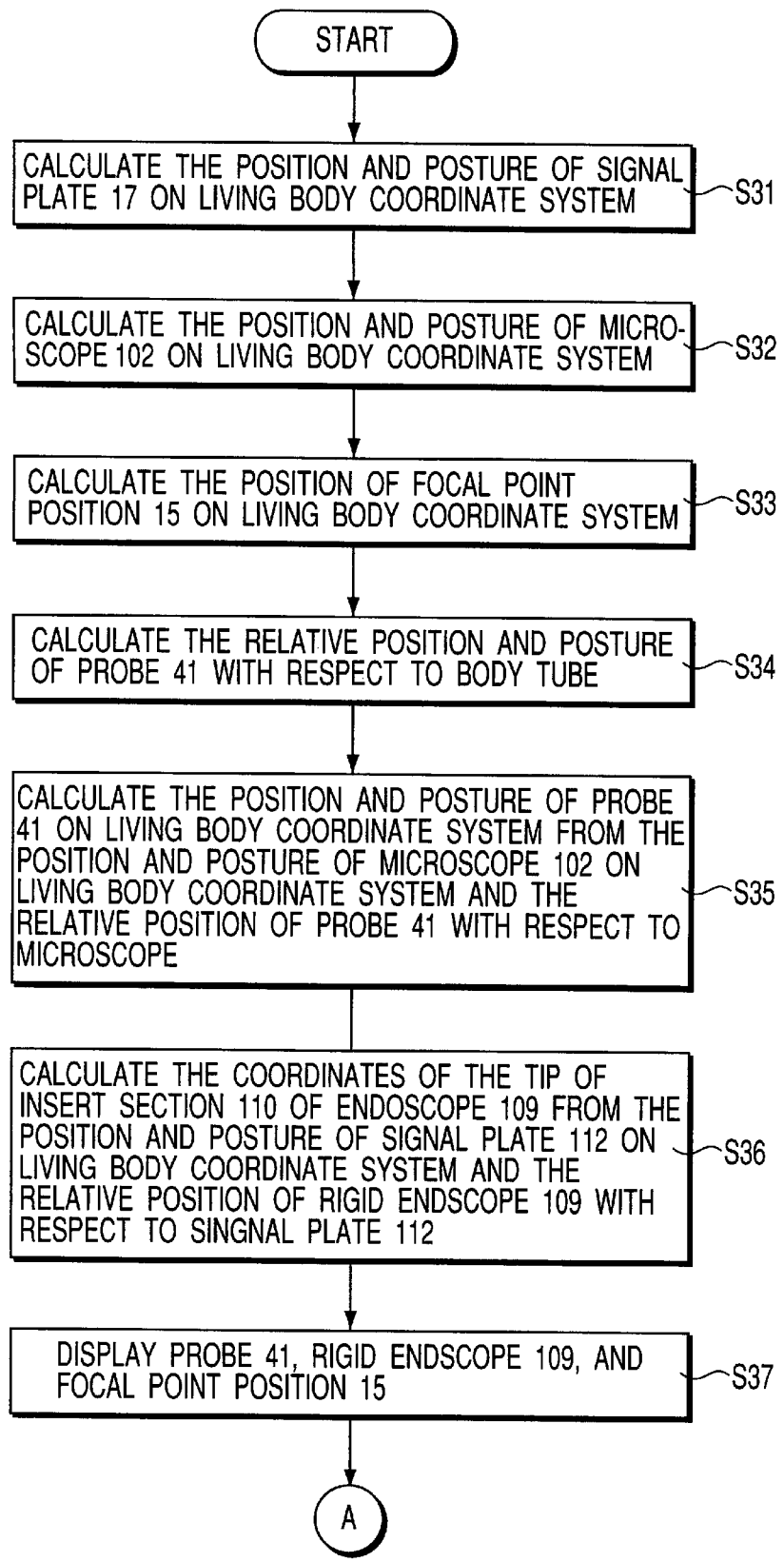

The operation of the second embodiment will be explained by reference to the flowcharts in FIGS. 11A and 11B. In the processes at step S31 to step S35 (which are the same as the processes at step S11 to S15 in FIG. 6), the microscope 102 is positioned and the position of the focal point position 15 on the living body coordinate system and the position and posture of the probe 41 on the living body coordinate system are calculated, as in the first embodiment.

The observation position of the rigid endoscope 109 can be sensed by the digitizer 30 sensing the LEDS 113a to 113d fixed integrally to the signal plate 112. At this time, the fact that the setting switch 114a has been selected is notified to the workstation 129. Recognizing that the signal plate 112 has been provided on the rigid endoscope 109, the workstation 129 calculates the tip of the insert section 110 of the rigid endoscope 109 from the previously recorded relative positions of the signal plate 112 and the rigid endoscope 109, and the coordinates of the signal plate 112 on the living body coordinate system (step S36).

Then, the probe 41, rigid endoscope 109, and focal point position 15 are displayed on the monitor 43 (step S39).

The luminous flux emitted from the operating site passes through the objective 11, enters the body tube 102, and passes through the variable power optical system 12. Then, the flux passes through the half mirror 100, which divides the flux into a flux passing through the half mirror 100 and traveling straight and a flux reflected and deflected at right angles by the half mirror 100. The flux traveling straight passes through the image-forming lenses 13a, 13b, which make images. The images pass through the eyepieces 14a, 14b and are observed.

The luminous flux reflected by the half mirror 100 is reflected upward again and passes through the pair of image-forming lenses 103a, 10b, which project images on the CCDs cameras 105a, 105b. The projected images are not only displayed on the 3D monitor 108 as a stereoscopic image but also outputted to the measuring unit 120. The magnification sensing means (not shown) outputs the magnification of the variable power optical system 12 to the workstation 129.

Next, the procedure for sensing the color markers 115, 116 with the CCD cameras 105a, 105b and determining the relative positions of the color markers to the body tube 102 will be explained.

When the color marker 115 is observed under the microscope and picked up by the CCD cameras 105a, 105b, the picked-up signal is processed by the measuring unit 120 and A/D converter 133 and the three-dimensional coordinates of the color marker 115 to the body tube 102 are sensed (step S38), as the digitizer did in the first embodiment. The same holds true for the color marker 116 provided at the tip of the probe 41.

Since the CCD cameras 105a, 105b are provided in specific positions on the microscope 102, the coordinates of the color marker 115 or 116 on the living body coordinate system are calculated by the workstation 129 from the installation positions of the signal plate 112 and CCD cameras 105a, 105b and the magnification (step S39).

When the sensor arm 112 is provided on another treating instrument, choosing either the setting switch 114b or setting switch 114c enables the tip of the treating instrument to navigate on the basis of information on the treating instrument previously recorded in the workstation 129.

With the second embodiment, even when the digitizer cannot pick up the LEDs on the signal plate 112 provided on the rigid endoscope 109, the pair of CCD cameras 105a, 105b built in the body tube 102 senses the color marker at the tip of the insert section and determines the position of the marker during treatment under the microscope, the position of the treating instrument can be sensed even near the complicated operating site as in the first embodiment. This produces the effects of shortening the operating time, alleviating the fatigue of the operator, and reducing the burden on the patient.

Use of sensing means composed of the CCD cameras 105a, 105b built in the microscope 102 makes it possible to sense the positions of treating instruments with color markers at their tips under the microscope.

Furthermore, because the CCD cameras 105a, 105b sense the image enlarged by the microscope, not only a smaller color marker but also a fine movement can be sensed reliably, which enables fine control of the tip of the treating instrument. This allows the operation to progress smoothly, which produces the effects of shortening the operating time, alleviating the fatigue of the operator, and reducing the burden on the patient.

Figure 12:
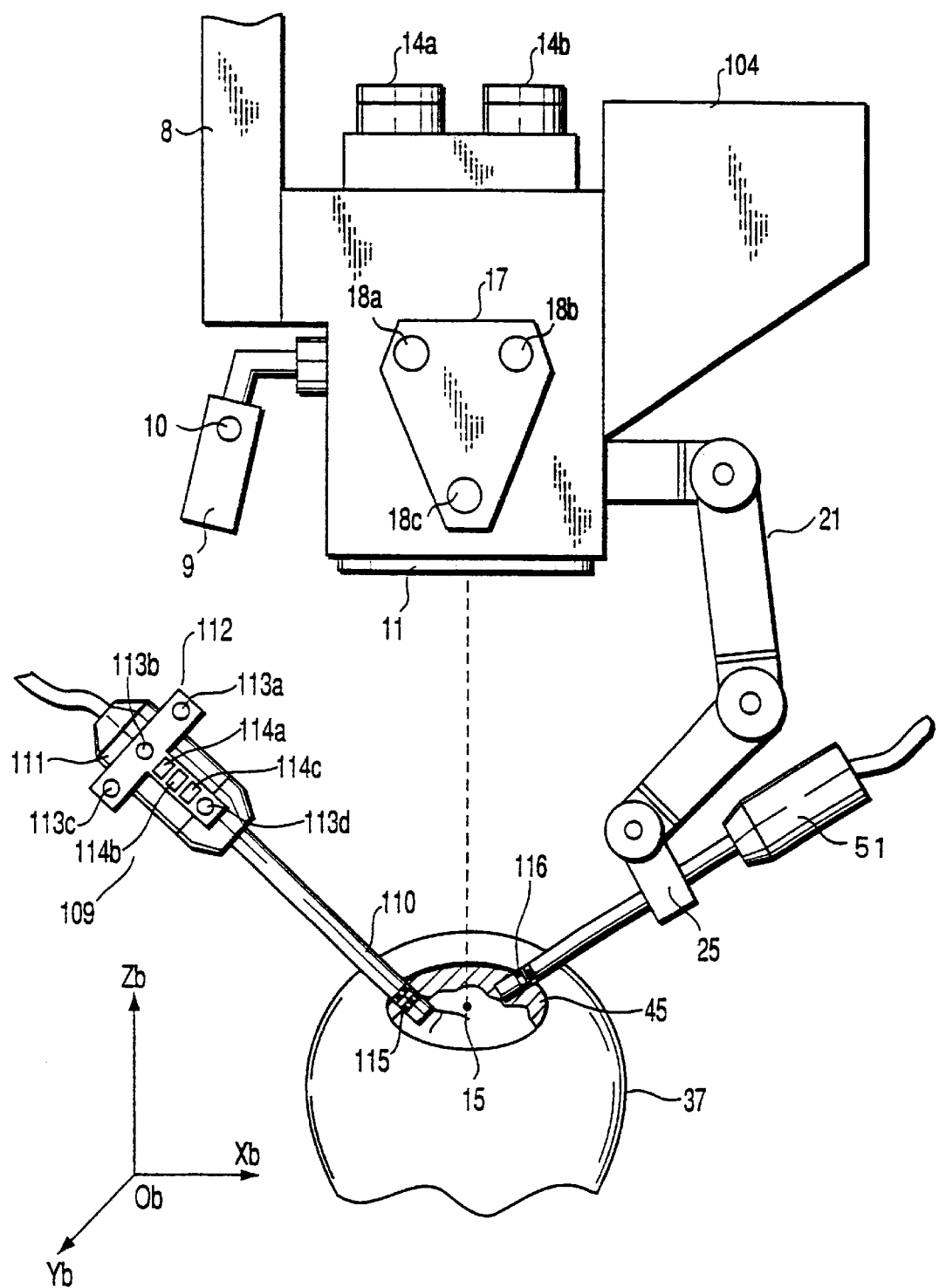
FIG. 12 is an enlarged side view of a microscope section according to a third embodiment of the present invention.

While in the second embodiment, an ultrasonic aspirator has been used as the treating instrument, a laser treating unit 51 acting as an energy treating instrument may be provided to the grip as shown in FIG. 12 according to the third embodiment.

On the basis of the tomographic image data, the robot manipulator 21 is driven so that laser projection may point to the target range as shown in FIG. 12. When it has pointed to the target range, the workstation 129 causes the laser treating unit 51 to emit laser. The emitted laser is projected on the target site and picked up by the pair of CCD cameras 105a, 105b built in the microscope 102 in the form of a single luminous point.

The luminous point picked up by the pair of CCD cameras 105a, 105b is processed as in the process of sensing the LEDs. This makes it possible to check the position where laser is actually being projected on the image based on the three-dimensional data. The depth of the focus is calculated from the three-dimensional image data and the intensity of the laser projection can be controlled according to the thickness of the focus.

Therefore, laser with unnecessary intensity is prevented from being projected on the focus, which assures reliable treatment and allows the operation to progress smoothly. This produces the effects of shortening the operating time, alleviating the fatigue of the operator, and reducing the burden on the patient.

Regarding the signal plate 112 mounted on the endoscope 109 of the second and the third embodiments, the operator can change the location of the signal plate 112 from the present instrument to another instrument to be navigated without taking the trouble to operate the workstation 129 to change the rigid endoscope 109 or the location of the signal plate during the operation. This enables the operator to change the setting easily at hand.

When the setting switches 114a to 114c on the signal plate of the second and the third embodiments are of the luminous type and the luminous section has an indication that allows the target treating instrument to be judged, the operator can check the presently selected treating instrument at hand.

This allows the operation to progress smoothly, which produces the effects of shortening the operating time, alleviating the fatigue of the operator, and reducing the burden on the patient.

Furthermore, the sensor arm need not be prepared for each treating instrument and can be shared by more than one treating instrument. As a result, the operator does not have to bear unnecessary cost.

Figure 13:
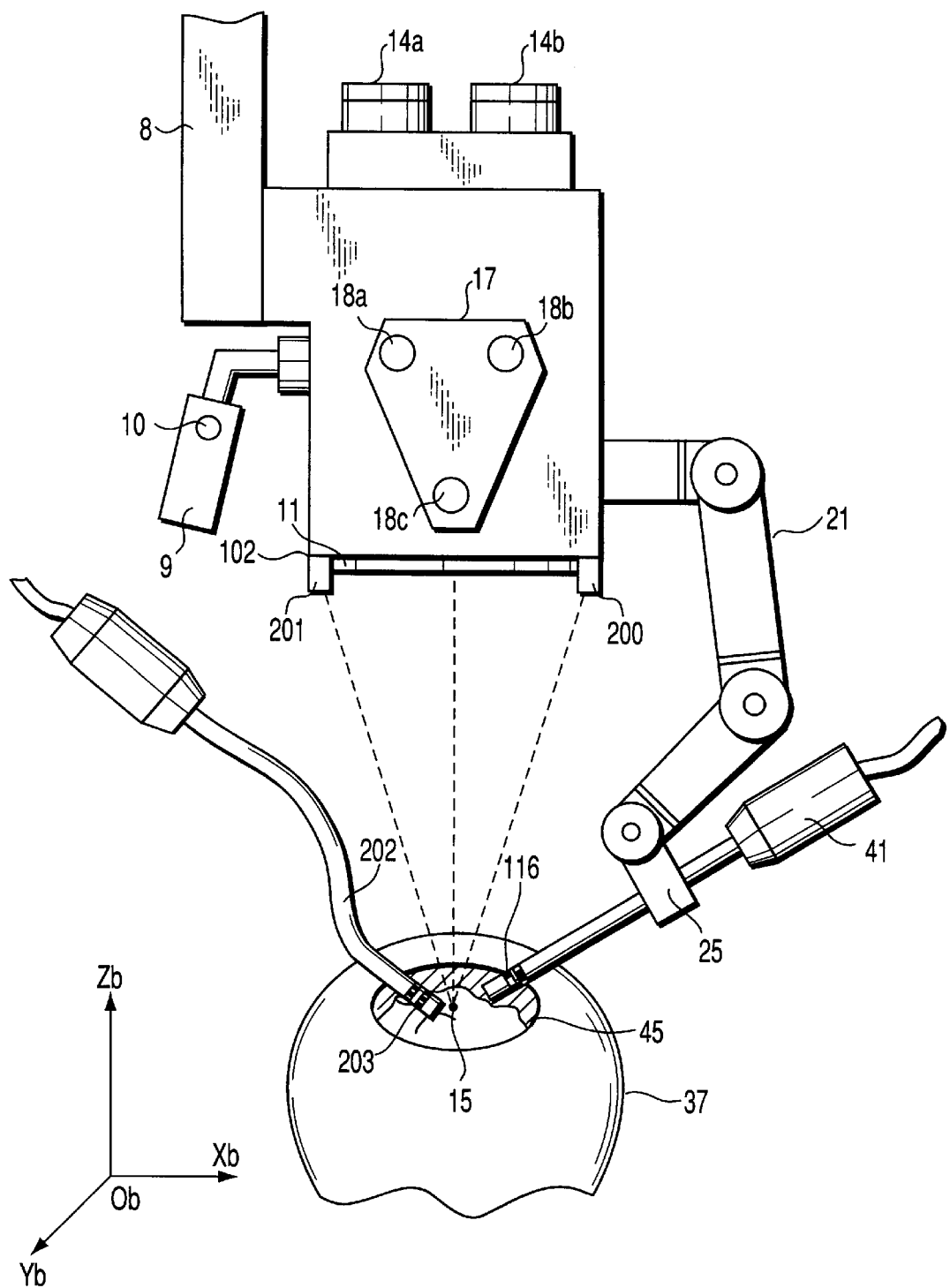
FIG. 13 is an enlarged side view of a microscope section according to a fourth embodiment of the present invention.

Next, a fourth embodiment of the present invention will be explained by reference to FIGS. 13 and 14. In FIGS. 13 to 14, the same parts as those in FIGS. 8 and 10 are indicated by the same reference symbols and a detailed explanation of them will not be given.

In FIG. 13, TV cameras 200 and 201 are provided on the bottom surface of the microscope 2 in such a manner that they pick up the operating site. The image pickup range of the TV cameras 200 and 201 is set wider than the observation range of the microscope. The image pickup optical system is completely independent of the optical system of the microscope.

Numeral 202 indicates an endoscope inserted into the operating site. A color marker 203 is provided at the tip of the endoscope 202, as in the first to third embodiments.

In FIG. 14, the TV cameras 200 and 201 are connected to the measuring unit 120 via CCUs 206 and 207, respectively.

The endoscope 202 is connected to a monitor 205 via an image processor 204.

The operation of the fourth embodiment will be explained. The image picked up by the CCD (not shown) of the endoscope 202 is converted into an image signal by the image processor 204 and displayed on the monitor 205.

The color marker 203 at the tip of the endoscope 202 inserted in the operating site is picked up by the TV cameras 200 and 201 and converted by the CCUs 206 and 207 into an image signal with a parallax. The converted signal is inputted to the measuring unit 120. The measuring unit 120 senses information on the position of the microscope 2 of the microscope on the operating site picked up by the digitizer 31 and the position of the color marker 203 on the endoscope 202 in the image pickup range of the TV cameras 200 and 201. The information is sent to the workstation 129. The workstation 129 calculates the observation positions of the microscope 2 and endoscope 202 and displays the result on the monitor 43.

As described above, with the fourth embodiment of the present invention, because the position sensing TV cameras 200, 201 are provided independently of the microscope, the position of the tip of the surgical instrument inserted in the vicinity of the operating site can always be sensed, regardless of the magnification of the microscope.

While in the fourth embodiment, an ultrasonic aspirator has been used as a treating instrument, another treating instrument may be installed in a similar manner, because the connection locations of the treating instrument to be installed and the robot manipulator have been determined.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical microscope comprising:
    a medical instrument;
    a first detector that is placed in a desired position, and that is configured to detect positional information of a microscope in three dimensions;
    a second detector that is mounted on the microscope at a predetermined position, and that is configured to detect positional information of the medical instrument with respect to the microscope in three dimensions; and a processor configured to calculate a three-dimensional position of the medical instrument with respect to the first detector based on the positional information of the microscope detected by the first detector and the positional information of the medical instrument detected by the second detector.

2. A surgical microscope according to claim 1, further comprising a memory configured to store a three-dimensional image including an image of an object to undergo a medical procedure performed using at least the medical instrument, wherein the processor correlates the positional information of the microscope with the three-dimensional image.

3. A surgical microscope according to claim 2, wherein the processor calculates a position of the microscope on three-dimensional coordinates correlated with the three-dimensional image.

4. A surgical microscope according to claim 3, further comprising a monitor configured to display an image based on the calculation performed by the processor, and wherein the monitor displays the image such that a focal point of the microscope is overlaid on the three-dimensional image.

5. A surgical microscope according to claim 3, wherein an origin of the three-dimensional coordinates is the object to undergo the medical procedure.

6. A surgical microscope according to claim 1, further comprising a memory configured to store a three-dimensional image including an image of an object to undergo a medical procedure performed using at least the medical instrument, wherein the processor correlates the medical instrument and the three-dimensional image based on the positional information of the microscope detected by the first detector and the positional information of the medical instrument detected by the second detector.

7. A surgical microscope according to claim 6, wherein the processor calculates a three-dimensional position of the medical instrument on three-dimensional coordinates correlated with the three-dimensional image.

8. A surgical microscope according to claim 7, wherein an origin of the three-dimensional coordinates is the object to undergo the medical procedure.

9. A surgical microscope according to claim 7, further comprising a monitor configured to display an image based on the calculation performed by the processor, and wherein the monitor displays the image such that a position of the microscope is overlaid on the three-dimensional image.

10. A surgical microscope according to claim 9, wherein:
the medical instrument comprises a functional part configured to conduct the medical procedure,
the three-dimensional position of the medical instrument calculated by the processor is a position of the functional part, and
the monitor displays the image such that at least the position of the functional part is overlaid on the three-dimensional image.

11. A surgical microscope according to claim 1, wherein:
the medical instrument is a first medical instrument,
the surgical microscope further comprises a second medical instrument,
the first detector detects positional information of the second medical instrument, and
the processor calculates a three-dimensional position of the second medical instrument with respect to the first detector based on the positional information of the second medical instrument detected by the first detector.

12. A surgical microscope according to claim 11, wherein the first detector optically detects the positional information of the second medical instrument.

13. A surgical microscope according to claim 12, wherein:
the first detector comprises a plurality of image pickup devices,
the second medical instrument comprises a plurality of light-emitting devices,
the plurality of image pickup devices receive light emitted from the plurality of light-emitting devices, and
the plurality of image pickup devices detect the positional information of the second medical instrument based on the received light.

14. A surgical microscope according to claim 11, further comprising a memory configured to store a three-dimensional image including an image of an object to undergo a medical procedure performed using at least the first medical instrument,
wherein the processor correlates the positional information of the second medical instrument with the three-dimensional image.

15. A surgical microscope according to claim 14, wherein the processor calculates the three-dimensional image of the second medical instrument on three-dimensional coordinates correlated with the three-dimensional image.

16. A surgical microscope according to claim 10, further comprising a monitor configured to display an image based on the calculation performed by the processor, and wherein the monitor displays the image such that the position of the second medical instrument is overlaid on the three-dimensional image.

17. A surgical microscope according to claim 16, wherein:
the second medical instrument comprises a functional part configured to conduct the medical procedure,
the three-dimensional position of the second medical instrument calculated by the processor is a position of the functional part,
the monitor displays the image such that at least the position of the functional part is overlaid on the three-dimensional image.

18. A surgical microscope according to claim 11, further comprising:
a memory configured to store a three-dimensional image including an image of an object to undergo a medical procedure performed using at least the first medical instrument; and
a monitor configured to display an image based on the calculation performed by the processor, wherein the monitor displays the image such that positions of both the first and second medical instruments are overlaid on the three-dimensional image.

19. A surgical microscope according to claim 11, further comprising:
a memory configured to store a three-dimensional image including an image of an object to undergo a medical procedure performed using at least the first medical instrument; and
a monitor configured to display an image based on the calculation performed by the processor, wherein the monitor displays the image such that a position of the second medical instrument is overlaid on the three-dimensional image.

20. A surgical microscope according to claim 1, wherein:
the medical instrument is a first medical instrument,
the surgical microscope further comprises a second medical instrument, the second detector detects positional information of the second medical instrument, and the processor calculates a three-dimensional position of the second medical instrument with respect to the second detector based on the positional information of the second medical instrument detected by the second detector.

21. A surgical microscope according to claim 20, wherein the second detector optically detects the positional information of the second medical instrument.

22. A surgical microscope according to claim 21, wherein:

the second detector comprises a plurality of image pickup devices, the second medical instrument comprises an index, and the plurality of image pickup devices capture the index as an image and detect positional information of the second medical instrument.

23. A surgical microscope according to claim 20, further comprising a memory configured to store a three-dimensional image including an image of an object to undergo a medical procedure performed using at least the first medical instrument, wherein the processor correlates the positional information of the second medical instrument with the three-dimensional image.

24. A surgical microscope according to claim 23, wherein the processor calculates the three-dimensional position of the second medical instrument on three-dimensional coordinates correlated with the three-dimensional image.

25. A surgical microscope according to claim 24, further comprising a monitor configured to display an image based on the calculation performed by the processor, and wherein the monitor displays the image such that the position of the second medical instrument is overlaid on the three-dimensional image.

26. A surgical microscope according to claim 25, wherein;

the second medical instrument comprises a functional part configured to conduct the medical procedure, the three-dimensional position of the second medical instrument calculated by the processor is a position of the functional part, the monitor displays the image such that at least the position of the functional part is overlaid on the three-dimensional image.

27. A surgical microscope according to claim 20, further comprising:

a memory configured to store a three-dimensional image including an image of an object to undergo a medical procedure performed using at least the first medical instrument; and a monitor configured to display an image based on the calculation performed by the processor, wherein the monitor displays the image such that positions of both the first and second medical instruments are overlaid on the three-dimensional image.

28. A surgical microscope according to claim 20, further comprising:

a memory configured to store a three-dimensional image including an image of an object to undergo a medical procedure performed using at least the first medical instrument; and a monitor configured to display an image based on the calculation performed by the processor, wherein the monitor displays the image such that a position of the second medical instrument is overlaid on the three-dimensional image.

29. A surgical microscope according to claim 20, further comprising an optical system provided for the second detector that is configured to obtain the positional information of the second medical instrument wherein at least one part of the optical system is shared with an observation optical system of the microscope.

30. A surgical microscope according to claim 20, wherein the second detector is arranged on a periphery of an optical axis of the observation optical system of the microscope.

31. A surgical microscope according to claim 1, wherein the first detector optically detects the positional information of the microscope.

32. A surgical microscope according to claim 31, wherein:

the first detector comprises a plurality of image pickup devices, the microscope comprises a plurality of light-emitting devices, the plurality of image pickup devices receive light emitted by the plurality of light-emitting devices, and the plurality of image pickup devices detect the positional information of the microscope based on the received light.

33. A surgical microscope according to claim 1, wherein the second detector optically detects the positional information of the medical instrument.

34. A surgical microscope according to claim 33, wherein:

the second detector comprises a plurality of image pickup devices, the medical instrument comprises an index, and the plurality of image pickup devices of the second detector capture the index as an image and detect the positional information of the medical instrument.

35. A surgical microscope according to claim 34, wherein:

the medical instrument is a first medical instrument, the index is a first index, the plurality of image pickup devices are capable of distinguishing colors, the surgical microscope further comprises a second medical instrument, the second medical instrument comprises a second index, a color of which is different from a color of the first index, and the plurality of image pickup devices capture the second index as an image and detect positional information of the second medical instrument.

36. A surgical microscope according to claim 35, wherein:

the first detector comprises a plurality of image pickup devices, the second medical instrument comprises a plurality of light-emitting devices, the plurality of image pickup devices of the first detector detect the positional information of the second medical instrument based on light received from the light-emitting devices, and the processor calculates a three-dimensional position of the second medical instrument with respect to the first detector based on the positional information of the second medical instrument detected by one of the first detector and the second detector.

37. A surgical microscope according to claim 34, further comprising an optical system provided among the plurality of image pickup devices of the second detector and the index of the medical instrument, and wherein at least one part of the optical system is shared with an observation optical system of the microscope.

38. A surgical microscope according to claim 1, wherein:

the second detector comprises a holder configured to hold the medical instrument and an actuator configured to move the medical instrument, the actuator couples the holder and the microscope, and the second detector detects a displacement distance of the actuator.

39. A surgical microscope according to claim 38, wherein:

the medical instrument comprises a functional part configured to conduct a medical procedure, the actuator comprises a plurality of arms, a plurality of joints configured to couple the plurality of arms in an operative manner, and motors respectively provided for the plurality of joints, and the second detector comprises an encoder configured to detect respective rotation amounts of the plurality of joints, which are based on driving of the motors.

40. A surgical microscope according to claim 38, further comprising:

a monitor configured to display a three-dimensional image including an image of an object to undergo a medical procedure performed using at least the first medical instrument;

a pointer configured to specify a desired position in the three-dimensional image displayed on the monitor; and a pointer moving section configured to move the pointer on the monitor, and wherein the processor carries out calculation for moving the medical instrument to the position specified by the pointer, and the actuator moves the medical instrument based on a calculation result provided by the processor.

41. A surgical microscope according to claim 1, wherein the first detector is separated from the microscope.

42. A surgical microscope according to claim 1, wherein the medical instrument comprises a functional part configured to conduct a medical procedure.

43. A surgical microscope according to claim 1, wherein:

the first detector is a first medical instrument, the surgical microscope further comprises a second medical instrument used for conducting a medical procedure, and positional information of the second medical instrument is detected by one of the first detector and the second detector.

44. A surgical microscope according to claim 1, further comprising a monitor configured to display a three-dimensional image including an image of an object to undergo a medical procedure performed using at least the first medical instrument, wherein the monitor displays the image such that the position of the medical instrument is overlaid on the three-dimensional image based on a calculation result provided by the processor.

45. A surgical microscope according to claim 1, wherein:

the second detector comprises a robotic manipulator which operates in accordance with a desired input signal, and the robotic manipulator holds the medical instrument and is attached to the microscope at a predetermined position.

46. A surgical microscope comprising:

a medical instrument;

a first detector configured to detect positional information of the medical instrument in three dimensions;

a body to which the first detector is attached;

a second detector configured to detect positional information of the body in three dimensions; and a processor for calculating a three-dimensional position of the medical instrument with respect to the second detector based on the positional information of the medical instrument detected by the first detector and the positional information of the body detected by the second detector.

47. A surgical microscope according to claim 46, wherein the second detector is separated from the microscope.

48. A surgical microscope according to claim 46, wherein:

the medical instrument is a first medical instrument, the surgical microscope further comprises a second medical instrument, and positional information of the second medical instrument is detected by one of the first detector and the second detector.

49. A surgical microscope according to claim 46, further comprising a monitor configured to display a three-dimensional image including an image of an object to undergo a medical procedure performed using at least the first medical instrument, wherein the monitor displays the image such that a position of the medical instrument is overlaid on the three-dimensional image based on a calculation result provided by the processor.

50. A surgical microscope according to claim 46, further comprising a memory configured to store a three-dimensional image including an image of an object to undergo a medical procedure performed using at least the medical instrument, wherein the processor correlates the positional information of the body with the three-dimensional image.

51. A surgical microscope according to claim 50, wherein the processor calculates a position of the body on three-dimensional coordinates correlated with the three-dimensional image.

52. A surgical microscope according to claim 51, wherein an origin of the three-dimensional coordinates is the object to undergo the medical procedure.

53. A surgical microscope according to claim 46, further comprising a memory configured to store a three-dimensional image including an image of an object to undergo a medical procedure performed using at least the medical instrument, wherein the processor correlates the medical instrument and the three-dimensional image based on the positional information of the medical instrument detected by the first detector and the positional information of the body detected by the second detector.

54. A surgical microscope according to claim 53, wherein the processor calculates the three-dimensional position of the medical instrument on three-dimensional coordinates correlated with the three-dimensional image.

55. A surgical microscope according to claim 54, wherein an origin of the three-dimensional coordinates is the object to undergo the medical procedure.

56. A surgical microscope according to claim 54, further comprising a monitor configured to display an image based on the calculation performed by the processor, and wherein the monitor displays the image such that the position of the medical instrument is overlaid on the three-dimensional image.

57. A surgical microscope according to claim 56, wherein:

the medical instrument comprises a functional part configured to conduct the medical procedure, the three-dimensional position of the medical instrument calculated by the processor is a position of the functional part, and the monitor displays the image such that at least the position of the functional part is overlaid on the three-dimensional image.

58. A surgical microscope according to claim 46, wherein:

the medical instrument is a first medical instrument, the surgical microscope further comprises a second medical instrument, the second detector detects positional information of the second medical instrument, and the processor calculates a three-dimensional position of the second medical instrument with respect to the second detector based on the positional information of the second medical instrument detected by the second detector.

59. A surgical microscope according to claim 58, wherein the second detector optically detects the positional information of the second medical instrument.

60. A surgical microscope according to claim 58, further comprising:

a memory configured to store a three-dimensional image including an image of an object to undergo a medical procedure performed using at least the first medical instrument; and a monitor configured to display an image based on the calculation performed by the processor, wherein the monitor displays the image such that positions of both the first and second medical instruments are overlaid on the three-dimensional image.

61. A surgical microscope according to claim 58, further comprising:

a memory configured to store a three-dimensional image including an image of an object to undergo a medical procedure performed using at least the first medical instrument; and a monitor configured to display an image based on the calculation performed by the processor, wherein the monitor displays the image such that a position of the second medical instrument is overlaid on the three-dimensional image.

62. A surgical microscope according to claim 46, wherein:

the medical instrument is a first medical instrument, the surgical microscope further comprises a second medical instrument, the first detector detects positional information of the second medical instrument, and the processor calculates a three-dimensional position of the second medical instrument with respect to the second detector based on the positional information of the second medical instrument detected by the first detector.

63. A surgical microscope according to claim 62, wherein the first detector optically detects the positional information of the second medical instrument.

64. A surgical microscope according to claim 62, further comprising:

a memory configured to store a three-dimensional image including an image of an object to undergo a medical procedure performed using at least the first medical instrument; and a monitor configured to display an image based on the calculation performed by the processor, wherein the monitor displays the image such that positions of both the first and second medical instruments are overlaid on the three-dimensional image.

65. A surgical microscope according to claim 62, further comprising:

a memory configured to store a three-dimensional image including an image of an object to undergo a medical procedure performed using at least the first medical instrument; and a monitor configured to display an image based on the calculation performed by the processor, wherein the monitor displays the image such that a position of the second medical instrument is overlaid on the three-dimensional image.

66. A surgical microscope according to claim 46, wherein the second detector optically detects the positional information of the body.

67. A surgical microscope according to claim 66, wherein:

the second detector comprises a plurality of image pickup devices, the microscope comprises a plurality of light-emitting devices, the plurality of image pickup devices receive light emitted by the plurality of light-emitting devices, and the plurality of image pickup devices detect positional information of the microscope based on the received light.

68. A surgical microscope according to claim 46, wherein the first detector optically detects the positional information of the medical instrument.

69. A surgical microscope according to claim 60, wherein:

the first detector comprises a plurality of image pickup devices, the medical instrument comprises an index, and the plurality of image pickup devices of the first detector capture the index as an image and detect the positional information of the medical instrument.

70. A surgical microscope according to claim 46, wherein:

the fist detector comprises a holder configured to hold the medical instrument and an actuator configured to move the medical instrument, the actuator couples the holder and the microscope, and the first detector detects a displacement distance of the actuator.

71. A surgical microscope according to claim 70, wherein:

the medical instrument comprises a functional part configured to conduct a medical procedure, the actuator comprises a plurality of arms, a plurality of joints configured to couple the plurality of arms in an operative manner, and motors respectively provided for the plurality of joints, and the first detector comprises an encoder configured to detect respective rotation amounts of the plurality of joints, which are based on driving of the motors.

72. A surgical microscope according to claim 46, wherein:

the first detector comprises a robotic manipulator which operates in accordance with a desired input signal, and the robotic manipulator holds the medical instrument and is attached to a predetermined position of the body.

* * * * *